(12) United States Patent
Nishina et al.

(10) Patent No.: US 8,053,733 B2
(45) Date of Patent: Nov. 8, 2011

(54) ELECTROMAGNETIC WAVE MEASURING APPARATUS

(75) Inventors: Shigeki Nishina, Miyagi (JP); Motoki Imamura, Miyagi (JP)

(73) Assignee: Advantest Corporation, Tokyo (JP)

( * ) Notice: Subject to any disclaimer, the term of this patent is extended or adjusted under 35 U.S.C. 154(b) by 33 days.

(21) Appl. No.: 12/616,992

(22) Filed: Nov. 12, 2009

(65) Prior Publication Data

US 2011/0075127 A1    Mar. 31, 2011

(30) Foreign Application Priority Data

Sep. 30, 2009    (JP) .................. 2009-228211

(51) Int. Cl.
G01J 5/02    (2006.01)
(52) U.S. Cl. .................. 250/341.1
(58) Field of Classification Search .......... 250/341.1, 250/341.3; 356/51
See application file for complete search history.

(56) References Cited

U.S. PATENT DOCUMENTS

| | | | |
|---|---|---|---|
| 5,428,447 A | 6/1995 | Toida | |
| 6,208,886 B1 * | 3/2001 | Alfano et al. | 600/473 |
| 6,828,558 B1 * | 12/2004 | Arnone et al. | 250/341.1 |
| 2001/0029436 A1 * | 10/2001 | Fukasawa | 702/117 |
| 2005/0023470 A1 * | 2/2005 | Ferguson et al. | 250/358.1 |
| 2006/0267848 A1 | 11/2006 | Nagashima | |
| 2008/0013071 A1 | 1/2008 | Tsumura et al. | |
| 2008/0217536 A1 | 9/2008 | Sekiguchi et al. | |
| 2010/0006758 A1 | 1/2010 | Sekiguchi et al. | |
| 2010/0288928 A1 | 11/2010 | Katagiri et al. | |

FOREIGN PATENT DOCUMENTS

| | | |
|---|---|---|
| JP | 6-50727 | 2/1994 |
| JP | 2002-98634 | 4/2002 |
| JP | 2006-133178 | 5/2006 |
| JP | 2006-275867 | 10/2006 |
| JP | 2008-249695 | 10/2008 |
| JP | 2009-192524 | 8/2009 |

OTHER PUBLICATIONS

Search report from P.C.T., mail date is Dec. 28, 2010.

* cited by examiner

*Primary Examiner* — David Porta
*Assistant Examiner* — Marcus Taningco
(74) *Attorney, Agent, or Firm* — Greenblum & Bernstein, P.L.C.

(57) ABSTRACT

A desired spatial resolution upon a measurement can be attained by making an electromagnetic wave including a terahertz wave (frequency thereof is equal to or more than 0.01 [THz], and equal to or less than 100 [THz]) incident to a device under test. An electromagnetic wave measurement device includes an incident lens which makes an electromagnetic wave to be measured having a frequency equal to or more than 0.01 [THz] and equal to or less than 100 [THz] incident to a device under a test while decreasing a beam diameter of the electromagnetic wave to be measured, a scanning stage which rotates, about a line orthogonal to an optical axis of the incident lens as a rotational axis, the device under the test or the optical axis, and an electromagnetic wave detector which detects the electromagnetic wave to be measured which has transmitted through the device under the test, where a coordinate on the optical axis of a position which gives the minimum value d of the beam diameter is different from a coordinate on the optical axis of the rotational axis.

14 Claims, 13 Drawing Sheets

ELECTROMAGNETIC WAVE MEASURING APPARATUS

BACKGROUND ART

1. Field of the Invention

The present invention relates to tomography using an electromagnetic wave (frequency thereof is equal to or more than 0.01 [THz], and equal to or less than 100 [THz]) (such as a terahertz wave (frequency thereof is equal to or more than 0.03 [THz], and equal to or less than 10 [THz]), for example).

2. Description of the Prior Art

There has conventionally been known a measurement device which irradiates a terahertz wave generated by a terahertz wave generator on a device under test, and uses a detector for terahertz wave to detect the terahertz wave which has transmitted through the device under test, thereby measuring the device under test.

As this type of a measurement device, there has been known a measurement device which includes a first optical system which condenses a terahertz wave generated by a generator for terahertz wave, and irradiates the condensed terahertz wave on a device under test, and a second optical system which makes the terahertz wave which has transmitted through the device under test incident to a detector for terahertz wave (refer to Abstract of Patent Document 1, for example).

(Patent Document 1) Japanese Laid-Open Patent Publication (Kokai) No. 2006-133178

SUMMARY OF THE INVENTION

On this occasion, the wavelength of the terahertz wave is approximately 100 μm to 2 mm, and is relatively long with respect to the device under test. As a result, a spot diameter of the terahertz wave on the device under test becomes large, and the spatial resolution upon the measurement of the device under test decreases.

In order to reduce the spot diameter of the terahertz wave on the device under test, a first optical system having a large numerical aperture may be used. In this case, the spatial resolution increases at a location of the spot of the terahertz wave on the device under test. However, the spatial resolution at a location apart from the spot of the terahertz wave on the device under test decreases on the contrary.

In this way, it is difficult for the measurement using an electromagnetic wave having a relatively long wavelength such as the terahertz wave to attain a desired spatial resolution upon measurement.

It is therefore an object of the present invention to attain a desired spatial resolution upon a measurement by making an electromagnetic wave including the terahertz wave (frequency thereof is equal to or more than 0.01 [THz], and equal to or less than 100 [THz]) incident to a device under test.

According to the present invention, a first electromagnetic wave measurement device includes: an incident optical system that makes an electromagnetic wave to be measured having a frequency equal to or more than 0.01 [THz] and equal to or less than 100 [THz] incident to a device under test while decreasing a beam diameter of the electromagnetic wave to be measured; a rotational drive unit that rotates, about a line orthogonal to an optical axis of the incident optical system as a rotational axis, the device under test or the optical axis; and an electromagnetic wave detector that detects the electromagnetic wave to be measured which has transmitted through the device under test, wherein a coordinate on the optical axis of a position at which the beam diameter is the minimum is different from a coordinate on the optical axis of the rotational axis.

According to the thus constructed first electromagnetic wave measurement device, an incident optical system makes an electromagnetic wave to be measured having a frequency equal to or more than 0.01 [THz] and equal to or less than 100 [THz] incident to a device under test while decreasing a beam diameter of the electromagnetic wave to be measured. A rotational drive unit rotates, about a line orthogonal to an optical axis of the incident optical system as a rotational axis, the device under test or the optical axis. An electromagnetic wave detector detects the electromagnetic wave to be measured which has transmitted through the device under test. A coordinate on the optical axis of a position at which the beam diameter is the minimum is different from a coordinate on the optical axis of the rotational axis.

According to the first electromagnetic wave measurement device of the present invention, a relationship $0.3\,r \leqq p \leqq 0.7\,r$ may hold where r denotes a radius of a cross section of the device under test on a plane orthogonal to the rotational axis, and p denotes a distance between the coordinate on the optical axis of the position at which the beam diameter is the minimum, and the coordinate on the optical axis of the rotational axis.

According to the first electromagnetic wave measurement device of the present invention, a relationship $p=0.5\,r$ may hold.

According to the first electromagnetic wave measurement device of the present invention, a cross section of the device under test on a plane orthogonal to the rotational axis is to be measured; and when p denotes a distance between the coordinate on the optical axis of the position at which the beam diameter is the minimum, and the coordinate on the optical axis of the rotational axis, p may be determined so that the spatial resolution upon the measurement of the cross section takes a desired value over the entire cross section.

According to the first electromagnetic wave measurement device of the present invention, a cross section of the device under test on a plane orthogonal to the rotational axis is to be measured; and a coordinate on the optical axis of a predetermined point of measurement on the cross section, which is different from an intersection between the cross section and the rotational axis, and the coordinate on the optical axis of the position at which the beam diameter is the minimum may be made to coincide with each other.

According to the first electromagnetic wave measurement device of the present invention, the incident optical system may be moved to a direction of the optical axis.

According to the first electromagnetic wave measurement device of the present invention, the device under test may be moved to a direction of the optical axis.

According to the first electromagnetic wave measurement device of the present invention, a focal distance of the incident optical system may be changed.

According to the first electromagnetic wave measurement device of the present invention, a cross section of the device under test on a plane orthogonal to the rotational axis is to be measured; and the cross section may be measured while the device under test or the optical axis is moved to a direction orthogonal to the optical axis and the rotational axis.

According to the present invention, a second electromagnetic wave measurement device includes: an incident optical system that makes an electromagnetic wave to be measured having a frequency equal to or more than 0.01 [THz] and equal to or less than 100 [THz] incident to a device under test while decreasing a beam diameter of the electromagnetic wave to be measured; a rotational drive unit that rotates, about a line orthogonal to an optical axis of the incident optical system as a rotational axis, the device under test or the optical axis; and an electromagnetic wave detector that detects the electromagnetic wave to be measured which has transmitted through the device under test, wherein: a plurality of types of a coordinate on the optical axis of a position at which the beam diameter is the minimum are set when a coordinate on the optical axis of the rotational axis is an origin; and the device under test is measured based on a result detected by the electromagnetic wave detector at the respective types of the coordinate.

According to the thus constructed second electromagnetic wave measurement device, an incident optical system makes an electromagnetic wave to be measured having a frequency equal to or more than 0.01 [THz] and equal to or less than 100 [THz] incident to a device under test while decreasing a beam diameter of the electromagnetic wave to be measured. A rotational drive unit rotates, about a line orthogonal to an optical axis of the incident optical system as a rotational axis, the device under test or the optical axis. An electromagnetic wave detector detects the electromagnetic wave to be measured which has transmitted through the device under test. A plurality of types of a coordinate on the optical axis of a position at which the beam diameter is the minimum are set when a coordinate on the optical axis of the rotational axis is an origin. The device under test is measured based on a result detected by the electromagnetic wave detector at the respective types of the coordinate.

According to the second electromagnetic wave measurement device of the present invention, the incident optical system may be moved to a direction of the optical axis.

According to the second electromagnetic wave measurement device of the present invention, the device under test may be moved to a direction of the optical axis.

According to the second electromagnetic wave measurement device of the present invention, a focal distance of the incident optical system may be changed.

According to the second electromagnetic wave measurement device of the present invention, a cross section of the device under test on a plane orthogonal to the rotational axis is to be measured; and the cross section may be measured while the device under test or the optical axis is moved to a direction orthogonal to the optical axis and the rotational axis.

According to the present invention, a third electromagnetic wave measurement device includes: an incident optical system that makes an electromagnetic wave to be measured having a frequency equal to or more than 0.01 [THz] and equal to or less than 100 [THz] incident to a device under test while decreasing a beam diameter of the electromagnetic wave to be measured; and an electromagnetic wave detector that detects the electromagnetic wave to be measured which has transmitted through the device under test, wherein: a plurality of types of a coordinate on the optical axis of a position at which the beam diameter is the minimum are set when a coordinate on the optical axis of a predetermined part of the device under test is an origin; and the device under test is measured based on a result detected by the electromagnetic wave detector at the respective types of the coordinate.

According to the thus constructed third electromagnetic wave measurement device, an incident optical system makes an electromagnetic wave to be measured having a frequency equal to or more than 0.01 [THz] and equal to or less than 100 [THz] incident to a device under test while decreasing a beam diameter of the electromagnetic wave to be measured. An electromagnetic wave detector detects the electromagnetic wave to be measured which has transmitted through the device under test. A plurality of types of a coordinate on the optical axis of a position at which the beam diameter is the minimum are set when a coordinate on the optical axis of a predetermined part of the device under test is an origin. The device under test is measured based on a result detected by the electromagnetic wave detector at the respective types of the coordinate.

According to the third electromagnetic wave measurement device of the present invention, the incident optical system may be moved to a direction of the optical axis.

According to the third electromagnetic wave measurement device of the present invention, the device under test may be moved to a direction of the optical axis.

According to the third electromagnetic wave measurement device of the present invention, a focal distance of the incident optical system may be changed.

According to the third electromagnetic wave measurement device of the present invention, a cross section of the device under test on a plane orthogonal to the optical axis is to be measured; and the cross section may be measured while the device under test or the optical axis is moved to two directions orthogonal to the optical axis and orthogonal to each other.

BEST MODE FOR CARRYING OUT THE INVENTION

A description will now be given of embodiments of the present invention with reference to drawings.

First Embodiment

Figure 1:
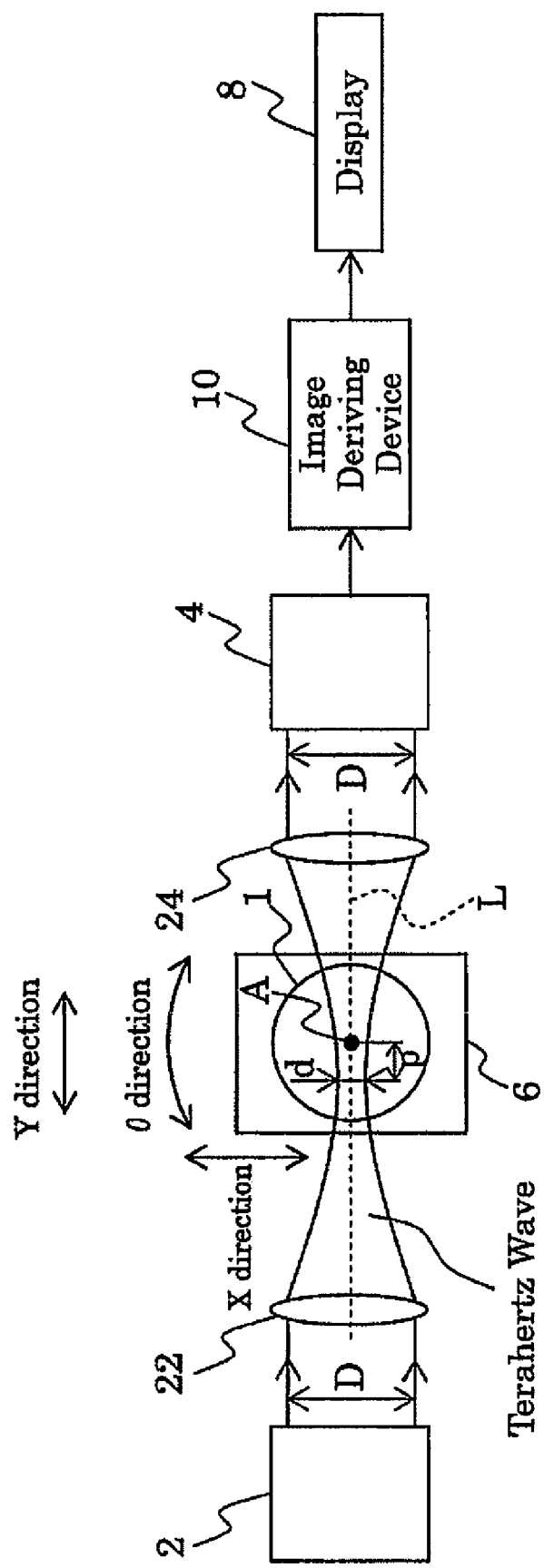
FIG. 1 is a diagram showing a configuration of an electromagnetic wave measurement device according to a first embodiment of the present invention.

FIG. 1 is a diagram showing a configuration of an electromagnetic wave measurement device according to a first embodiment of the present invention. The electromagnetic wave measurement device according to the first embodiment includes an electromagnetic wave output device 2, an electromagnetic wave detector 4, a scanning stage (rotational drive unit) 6, a display 8, an image deriving device 10, an incident lens (incident optical system) 22, and an objective lens 24. The electromagnetic wave measurement device is used for measuring a device under test (DUT) 1.

The electromagnetic wave output device 2 outputs an electromagnetic wave having a frequency equal to or more than 0.01 [THz] and equal to or less than 100 [THz] (hereinafter referred to as "electromagnetic wave to be measured") toward the DUT 1. The frequency of the electromagnetic wave output toward the DUT 1 includes a terahertz wave band (such as equal to or more than 0.03 [THz] and equal to or less than 10 [THz]). According to the embodiment of the present invention, it is assumed that a terahertz wave is employed as an example of the electromagnetic wave to be measured.

The terahertz wave output toward the DUT 1 is a type of light and a type of a beam. This terahertz wave is made incident to the incident lens (incident optical system) 22.

The incident lens (incident optical system) 22 is a convex lens, for example. The incident lens 22 makes the terahertz wave incident to the DUT while decreasing the beam diameter of the terahertz wave. For example, the beam diameter of the terahertz wave made incident to the incident lens 22 is D, and the minimum of the beam diameter is d (<D).

The terahertz wave made incident from the incident lens 22 to the DUT 1 transmits through the DUT 1. Then, the beam diameter of the terahertz wave gradually increases from d. The terahertz wave which has transmitted through the DUT 1 is made incident to the objective lens 24. The objective lens 24 changes the beam diameter of the terahertz wave which has transmitted through the DUT 1 to a constant value (such as D), and makes the terahertz wave incident to the electromagnetic wave detector 4.

It should be noted that an optical axis of the incident lens 22 and the objective lens 24 is denoted by L. An axis of rotational symmetry of the incident lens 22 and the objective lens 24 is the optical axis L. A direction of the extension of the optical axis L is denoted by Y direction.

The electromagnetic wave detector 4 detects the electromagnetic wave to be measured (such as a terahertz wave) which has transmitted through the DUT 1.

The scanning stage (rotational drive unit) 6 rotates the DUT 1 about a line A (which is a line orthogonal to the sheet of FIG. 1) orthogonal to the optical axis L as a rotational axis.

Figure 12:
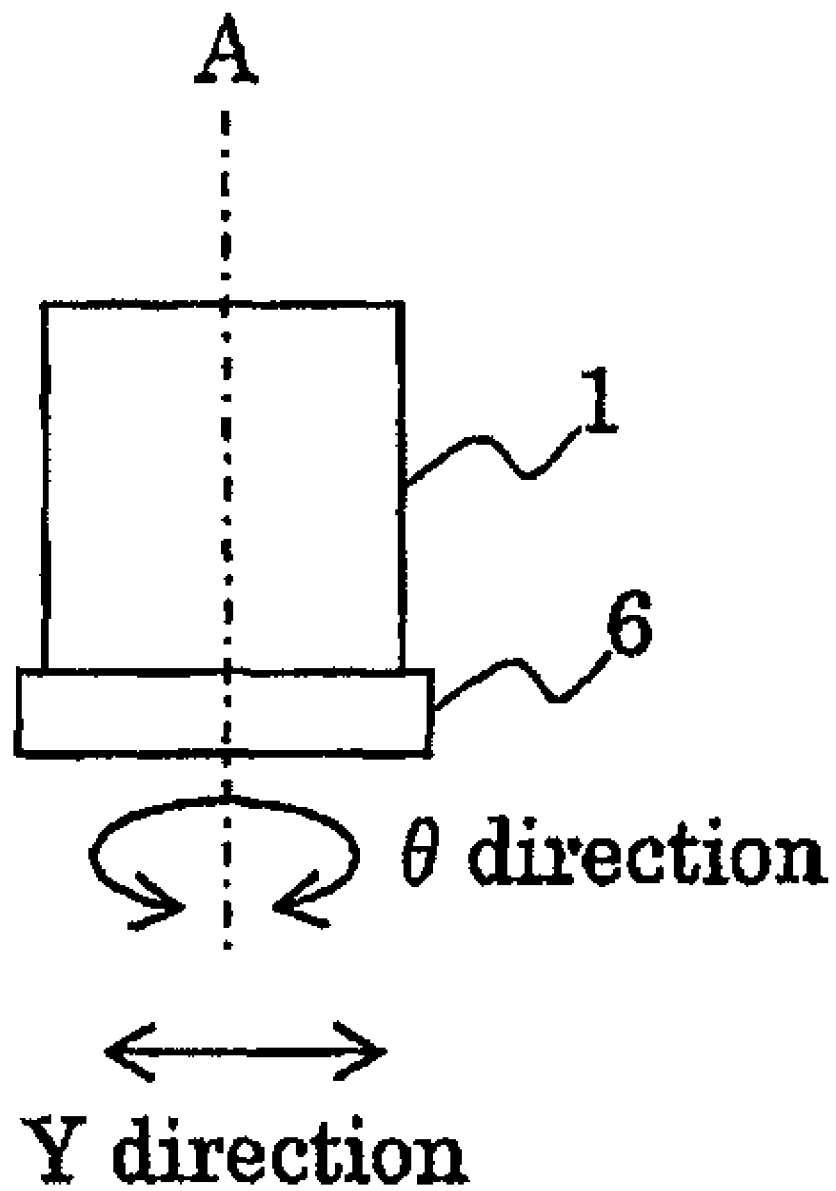
FIG. 12 is a front view of the DUT 1 and the scanning stage 6 according to the first embodiment of the present invention.

FIG. 12 is a front view of the DUT 1 and the scanning stage 6 according to the first embodiment of the present invention. The DUT 1 is placed on the scanning stage 6. When the scanning stage 6 rotates about the line A as the rotational axis, the DUT 1 also rotates about the line A.

Moreover, the electromagnetic wave measurement device measures a cross section of the DUT 1 on a plane orthogonal to the line A (rotational axis).

It should be noted that a position which gives the minimum value d of the beam diameter of the terahertz wave is displaced from the line A by a distance p. It is considered that a coordinate on the optical axis L of the position which gives the minimum value d of the beam diameter of the terahertz wave is different from a coordinate on the optical axis L of the line A (rotational axis) by the distance p.

A radius of a cross section of the DUT 1 on a plane orthogonal to the line A (rotational axis) is denoted by r. The distance p is then 0.5 r, for example. In the example shown in FIG. 1, the position which gives the minimum value d of the beam diameter of the terahertz wave is closer to the incident lens 22 than the line A (rotational axis). However, the position which gives the minimum value d of the beam diameter of the terahertz wave may be farther from the incident lens 22 than the line A (rotational axis).

A description will be given of a case in which the position which gives the minimum value d of the beam diameter of the terahertz wave is closer to the incident lens 22 than the line A (rotational axis), and p is 0.5 r. However, as long as a relationship $0.3\ r \leq p \leq 0.7\ r$ holds, it is expected that effects according to the first embodiment are provided.

Figure 5:
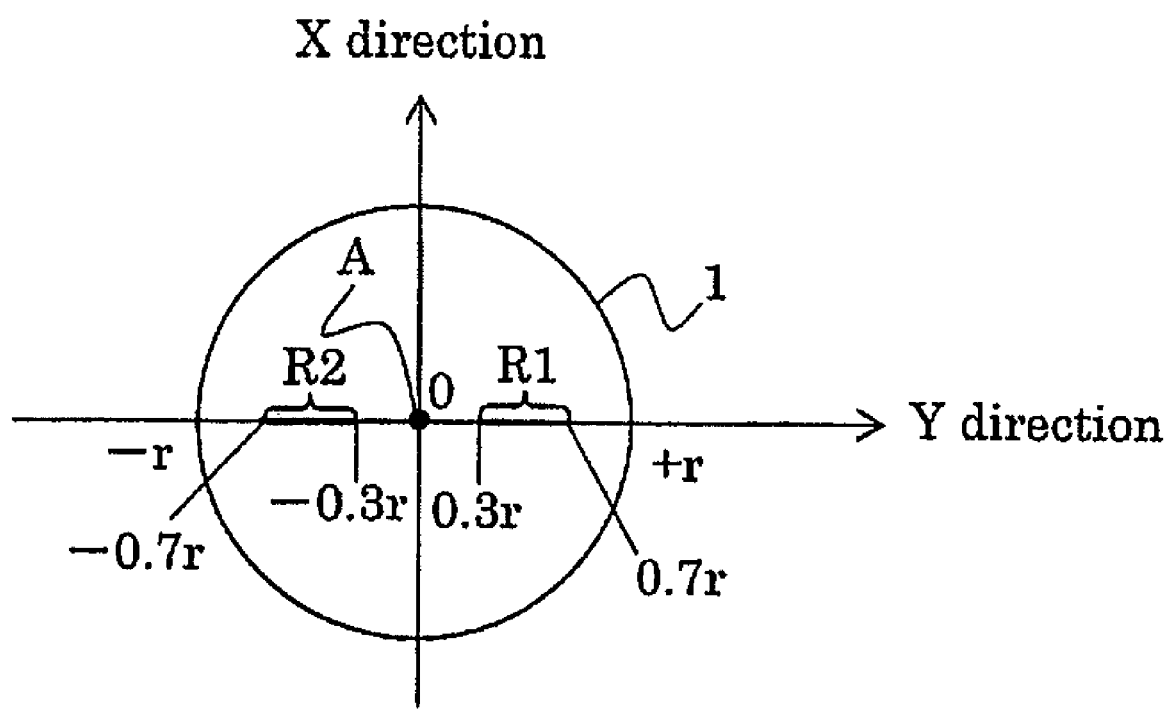
FIG. 5 is a cross sectional view of the DUT 1 for describing the example of the distance p according to the first embodiment.

FIG. 5 is a cross sectional view of the DUT 1 for describing the example of the distance p according to the first embodiment. The cross section of the DUT 1 ranges from −r to +r in terms of a Y coordinate (a coordinate on the optical axis L) when an intersection between the line A and the cross section is the origin. On this occasion, the position which gives the minimum value d of the beam diameter of the terahertz wave may be displaced by a distance equal to or more than 0.3 r and equal to or less than 0.7 r from the intersection between the line A and the cross section toward the objective lens 24 (may be set in a range R1: equal to or more than 0.3 r and equal to or less than 0.7 r in terms of the Y coordinate). Alternatively, the position which gives the minimum value d of the beam diameter of the terahertz wave may be displaced by a distance equal to or more than 0.3 r and equal to or less than 0.7 r from the intersection between the line A and the cross section toward the incident lens 22 (may be set in a range R2: equal to or more than −0.7 r and equal to or less than −0.3 r in terms of the Y coordinate).

It should be noted that the scanning stage 6 can be moved to an X direction (a direction orthogonal to the Y direction and the line A) and the Y direction. As a result, the DUT 1 can be moved to the X direction and the Y direction (direction in which the optical axis L extends).

The movement of the scanning stage 6 to the Y direction enables adjustment of the distance p (refer to FIG. 1). However, the distance p may be adjusted by moving the incident lens 22 to the Y direction. Moreover, the distance p may be adjusted by changing the focal distance of the incident lens 22 (it is assumed that the position which gives the minimum value d of the beam diameter is the focal point).

Figure 2:
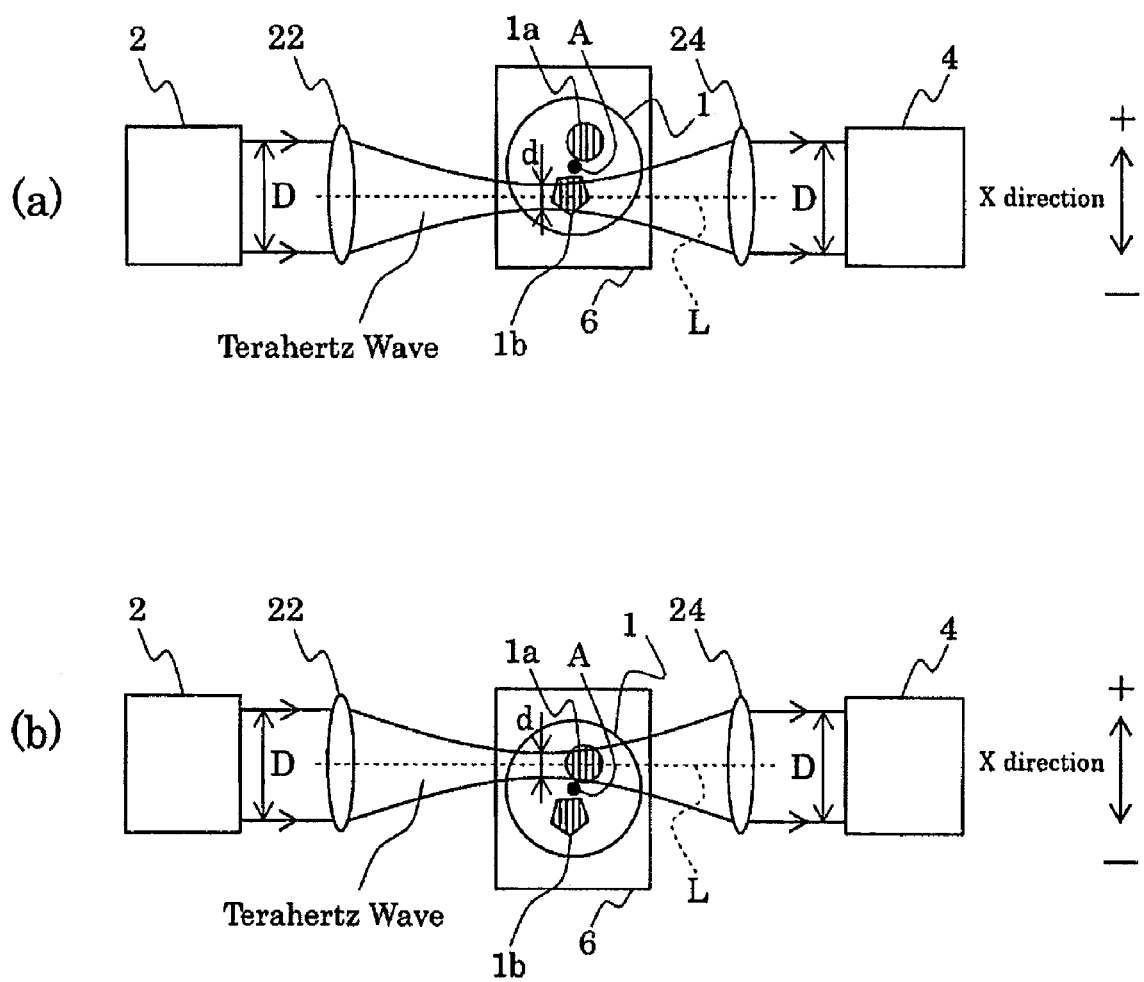
FIGS. 2(a) and 2(b) are plan views of the DUT 1, the electromagnetic wave output device 2, the incident lens 22, the objective lens 24, the electromagnetic wave detector 4, and the scanning stage 6 when the scanning stage 6 is moved to the X direction.

FIGS. 2(a) and 2(b) are plan views of the DUT 1, the electromagnetic wave output device 2, the incident lens 22, the objective lens 24, the electromagnetic wave detector 4, and the scanning stage 6 when the scanning stage 6 is moved to the X direction. It should be noted that the DUT 1 contains contents 1a and 1b.

Referring to FIG. 2(a), when the scanning stage 6 is moved to the +X direction (alternatively, the electromagnetic wave output device 2, the incident lens 22, the objective lens 24, and the electromagnetic wave detector 4 may be moved to the −X direction thereby moving the optical axis L to the −X direction) starting from the state in FIG. 1, the position which gives the minimum value d of the beam diameter of the terahertz wave is brought into a neighborhood of the content 1b.

Referring to FIG. 2(b), when the scanning stage 6 is moved to the −X direction (alternatively, the electromagnetic wave output device 2, the incident lens 22, the objective lens 24, and the electromagnetic wave detector 4 may be moved to the +X direction thereby moving the optical axis L to the +X direction) starting from the state in FIG. 1, the position which gives the minimum value d of the beam diameter of the terahertz wave is brought into a neighborhood of the content 1a.

Figure 3:
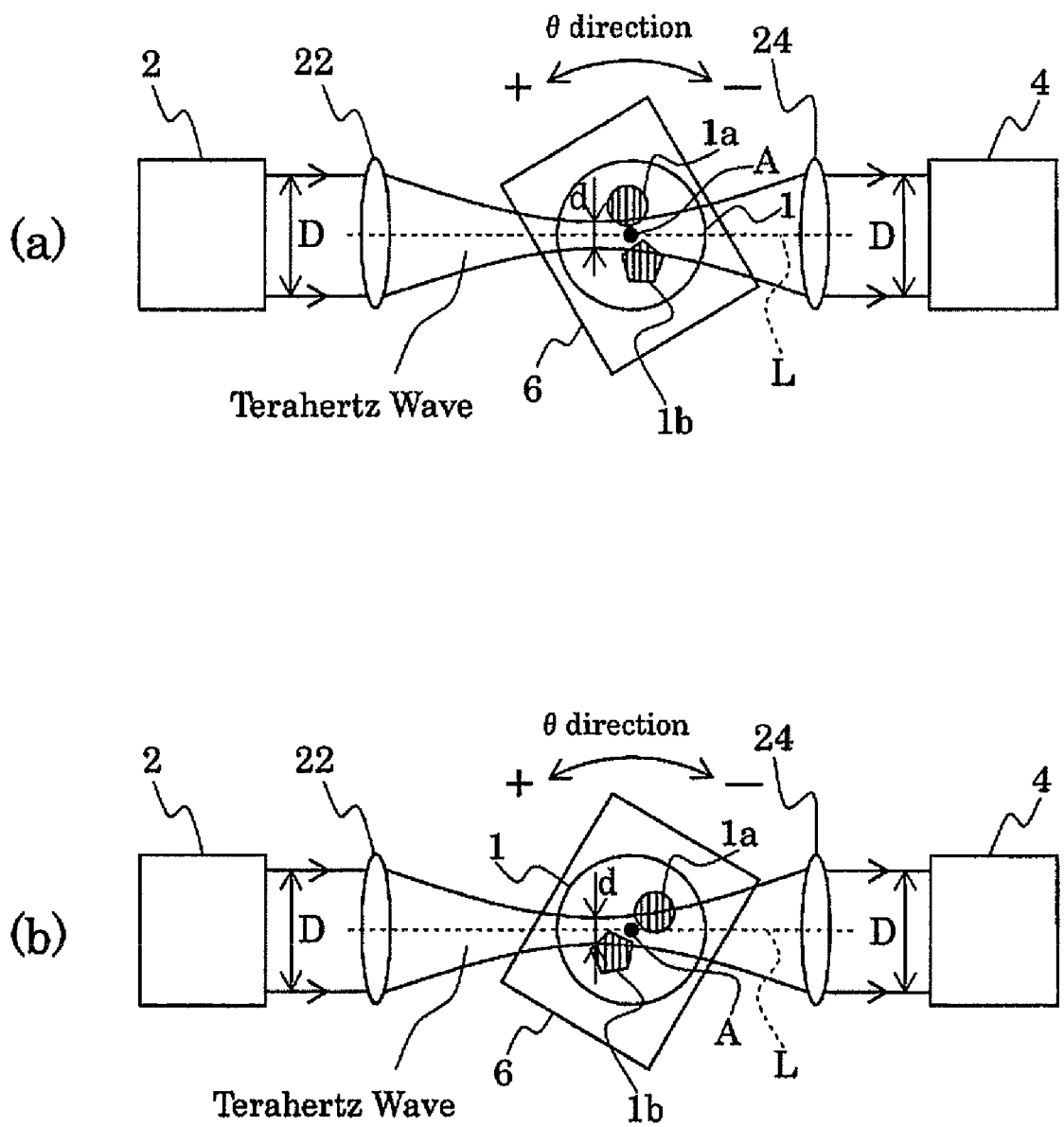
FIGS. 3(a) and 3(b) are plan views of the DUT 1, the electromagnetic wave output device 2, the incident lens 22, the objective lens 24, the electromagnetic wave detector 4, and the scanning stage 6 when the scanning stage 6 is rotated about the line A as the rotational axis.

FIGS. 3(a) and 3(b) are plan views of the DUT 1, the electromagnetic wave output device 2, the incident lens 22, the objective lens 24, the electromagnetic wave detector 4, and the scanning stage 6 when the scanning stage 6 is rotated about the line A as the rotational axis. It should be noted that the DUT 1 contains the contents 1a and 1b.

Referring to FIG. 3(a), when the scanning stage 6 is rotated in a +θ direction (alternatively, the electromagnetic wave output device 2, the incident lens 22, the objective lens 24, and the electromagnetic wave detector 4 may be rotated in a −θ direction thereby rotating the optical axis L in the −θ direction) starting from the state in FIG. 1, the position which gives the minimum value d of the beam diameter of the terahertz wave is brought into a neighborhood of the content 1a.

Referring to FIG. 3(b), when the scanning stage 6 is rotated in the −θ direction (alternatively, the electromagnetic wave output device 2, the incident lens 22, the objective lens 24, and the electromagnetic wave detector 4 may be rotated in the +θ direction thereby rotating the optical axis L in the +θ direction) starting from the state in FIG. 1, the position which gives the minimum value d of the beam diameter of the terahertz wave is brought into a neighborhood of the content 1b.

When a cross section of the DUT 1 on a plane orthogonal to the line A is measured, the movement to the X direction and the rotation about the line A of the scanning stage 6 are carried out at the same time. As a result, the DUT 1 is moved to the X direction (the direction orthogonal to the optical axis L and the line A (rotational axis)), and also rotated about the line A. Alternatively, the optical axis L is moved to the X direction, and is also rotated about the line A (refer to a variation of the first embodiment (FIG. 13)).

FIGS. 4(a) and 4(b) are plan views of the DUT 1, the electromagnetic wave output device 2, the incident lens 22, the objective lens 24, the electromagnetic wave detector 4, and the scanning stage 6 when the scanning stage 6 is moved to the X direction, and is also rotated about the line A for measuring a cross section of the DUT 1 on a plane orthogonal to the line A according to the first embodiment. It should be noted that the DUT 1 contains the contents 1a and 1b.

FIG. 4(a) is a plan view when the scanning stage 6 is moved to the −X direction and is also rotated in the +θ direction from the state in FIG. 1. The position which gives the minimum value d of the beam diameter of the terahertz wave is brought into a neighborhood of the content 1a. It should be noted that the electromagnetic wave output device 2, the incident lens 22, the objective lens 24, and the electromagnetic wave detector 4 may be moved to the +X direction, and may also be rotated in the −θ direction (which moves the optical axis L to the +X direction, and rotates −θ direction), and this brings about the same state as shown in FIG. 4(a).

FIG. 4(b) is a plan view when the scanning stage 6 is moved to the +X direction and is also rotated in the −θ direction from the state in FIG. 1. The position which gives the minimum value d of the beam diameter of the terahertz wave is brought into a neighborhood of the content 1b. It should be noted that the electromagnetic wave output device 2, the incident lens 22, the objective lens 24, and the electromagnetic wave detector 4 may be moved to the −X direction, and may also be rotated in the +θ direction (which moves the optical axis L to the −X direction, and rotates in the +θ direction), and this brings about the same state as shown in FIG. 4(b).

When the Y coordinate of the position which gives the minimum value d of the beam diameter of the terahertz wave is made coincident with the Y coordinate of the intersection between the line A (rotational axis) and the cross section of the DUT 1 as in the conventional CT (computer tomography), the Y coordinate (coordinate on the optical axis L) of the position which gives the minimum value d of the beam diameter of the terahertz wave remains coincident with the Y coordinate of the intersection between the line A (rotational axis) and the cross section of the DUT 1. As a result, the position which gives the minimum value d of the beam diameter of the terahertz wave moves only to certain specific portions on the cross section of the DUT 1.

However, according to the first embodiment, referring to FIGS. 4(a) and 4(b), it is appreciated that the position which gives the minimum value d of the beam diameter of the terahertz wave moves to various portions on the cross section of the DUT 1.

The image deriving device 10 derives an image of the cross section of the DUT 1 on the plane orthogonal to the line A. The derivation of the image may be based on the derivation of an image by the widely-known filtered back-projection.

The display 8 shows the image derived by the image deriving device 10. The derived image is numerical data on the two-dimensional cross section of the DUT 1, and a two-dimensional tomographic image of the DUT 1 is shown by associating the numerical data with predetermined colors. It should be noted that a widely known method may be properly employed as the method for displaying a two-dimensional tomographic image based on numerical data.

A description will now be given of an operation of the first embodiment.

First, the DUT 1 is fixed to the scanning stage 6. Then, the scanning stage 6 is not moved to the direction of the line A, but is fixed, and is moved to the Y direction, thereby adjusting the distance p (refer to FIG. 1) (p=0.5 r, for example). The scanning stage 6 is then moved to the X direction, and is also rotated about the line A.

On this occasion, the electromagnetic wave having the frequency equal to or more than 0.01 [THz] and equal to or less than 100 [THz] (such as the terahertz wave) is output from the electromagnetic wave output device 2 toward the DUT 1. The terahertz wave output toward the DUT 1 is made incident to the DUT 1 while the beam diameter is decreased by the incident lens 22.

Figure 4:
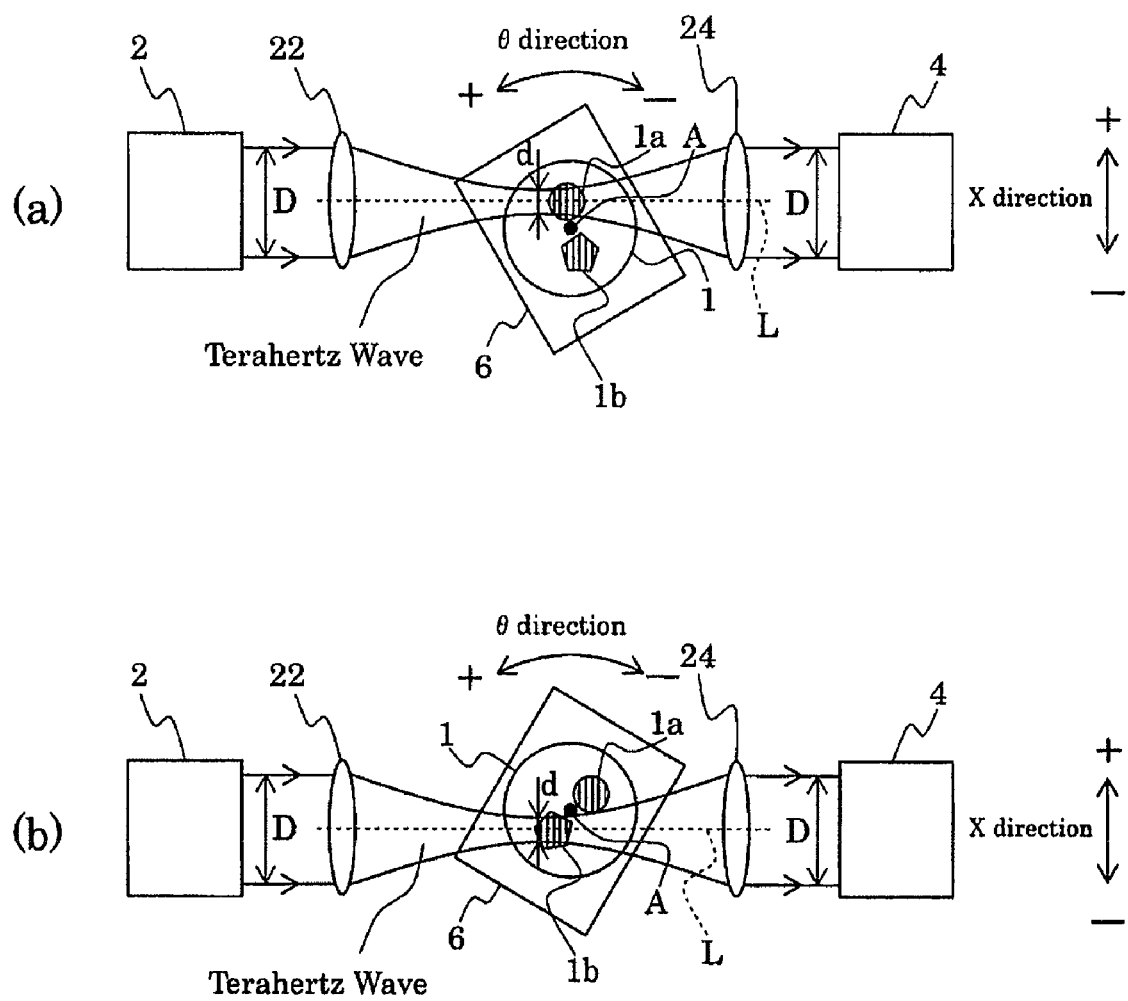
FIGS. 4(a) and 4(b) are plan views of the DUT 1, the electromagnetic wave output device 2, the incident lens 22, the objective lens 24, the electromagnetic wave detector 4, and the scanning stage 6 when the scanning stage 6 is moved to the X direction, and is also rotated about the line A for measuring a cross section of the DUT 1 on a plane orthogonal to the line A according to the first embodiment.

On this occasion, referring to FIG. 4, the position which gives the minimum value d of the beam diameter of the terahertz wave moves to the neighborhood of the content 1a (refer to FIG. 4(a)) or the neighborhood of the content 1b (refer to FIG. 4(b)) as the scanning stage 6 moves and rotates.

The terahertz wave transmits through the DUT 1, the beam diameter gradually increases from d, and the terahertz wave is made incident to the objective lens 24. The objective lens 24 changes the beam diameter of the terahertz wave which has transmitted through the DUT 1 to a constant value (such as D), and makes the terahertz wave incident to the electromagnetic wave detector 4.

The electromagnetic wave which has transmitted through the DUT 1 is detected via the objective lens 24 by the electromagnetic wave detector 4. In this way, the DUT 1 is scanned.

The result detected by the electromagnetic wave detector 4 is fed to the image deriving device 10, and derives the image of the cross section of the DUT 1 on the plane orthogonal to the line A. The image derived by the image deriving device 10 is shown by the display 8.

When a certain cross section of the DUT 1 has been measured, the scanning stage 6 is moved to the direction of the line A by a predetermined distance, and is fixed, and the DUT 1 is scanned for measurement of a further cross section.

According to the first embodiment, the coordinate on the optical axis L of the position which gives the minimum value d of the beam diameter of the terahertz wave is displaced from the coordinate on the optical axis L of the line A (rotational axis) by the distance p (such as 0.5 r). As a result, referring to FIG. 4, when the DUT 1 is being scanned, the position which gives the minimum value d of the beam diameter of the terahertz wave moves to various portions on a cross section of the DUT 1.

The position which gives the minimum value d of the beam diameter of the terahertz wave is a position having a high spatial resolution for measuring the cross section. Therefore, if the position which gives the minimum value d of the beam diameter of the terahertz wave moves to various portions of the cross section of the DUT 1, the spatial resolution increases for the measurement of the various portions of the cross section of the DUT 1.

Thus, when a cross section of the DUT 1 is measured, the spatial resolution can be increased approximately uniformly over the entire cross section.

It is considered that the distance p is determined so that the spatial resolution for measuring a cross section of the DUT 1 has a desired value over the entire cross section (such as p=0.5 r or p is equal to or more than 0.3 r and equal to or less than 0.7 r).

Moreover, the description has been given assuming that the DUT 1 is placed on the scanning stage 6. However, not the DUT 1, but the electromagnetic wave output device 2, the incident lens 22, the objective lens 24 and the electromagnetic wave detector 4 can be placed on the scanning stage 6.

Figure 13:
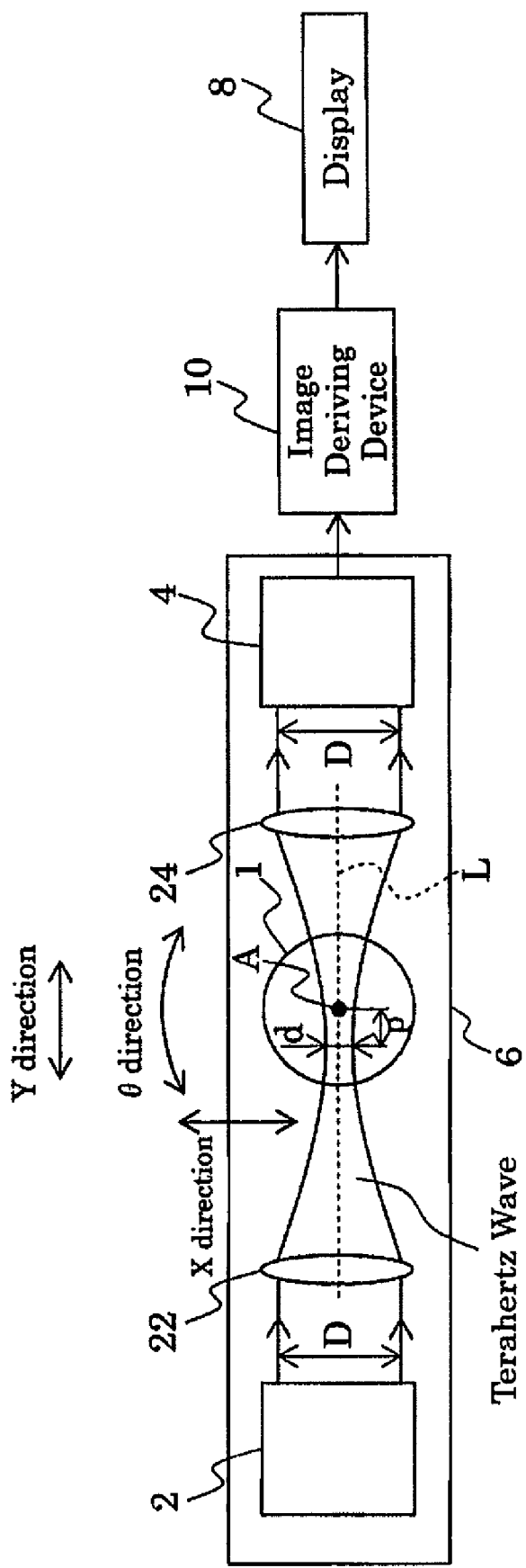
FIG. 13 is a diagram showing a configuration of the electromagnetic wave measurement device according to the variation of the first embodiment of the present invention.

FIG. 13 is a diagram showing a configuration of the electromagnetic wave measurement device according to the variation of the first embodiment of the present invention. The electromagnetic wave measurement device according to the variation of the first embodiment is configured such that the electromagnetic wave output device 2, the incident lens 22, the objective lens 24 and the electromagnetic wave detector 4 are placed on the scanning stage 6 (the other configuration is the same as that of the first embodiment).

According to the variation of the first embodiment, by moving the scanning stage 6 to the X and Y directions, the optical axis L can be moved to the X and Y directions. Moreover, by rotating the scanning stage 6 about the line A as a rotational axis, the optical axis L can be rotated about the line A as a rotational axis.

Second Embodiment

The electromagnetic wave measurement device according to a second embodiment is different from the first embodiment in that, when the DUT 1 is scanned, a coordinate on the optical axis L of a predetermined point of measurement B (refer to FIG. 6) on a cross section of the DUT 1 and the coordinate on the optical axis L of the position which gives the minimum value d of the beam diameter coincide with each other.

Figure 6:
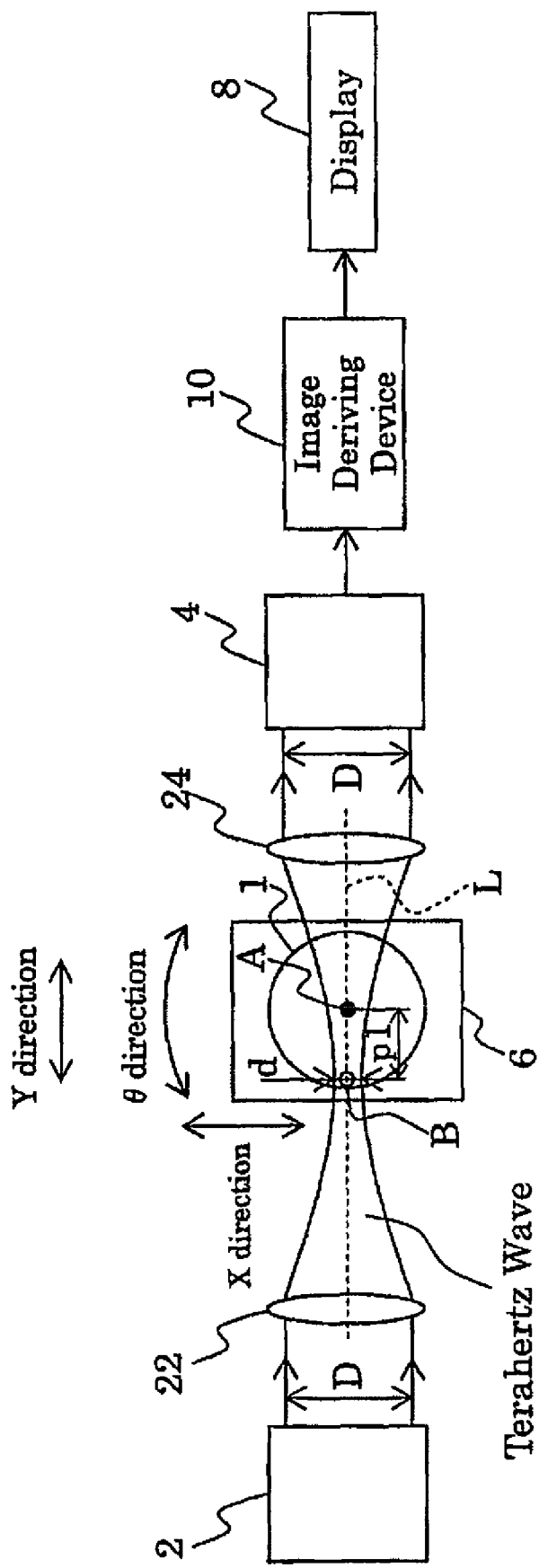
FIG. 6 is a diagram showing a configuration of the electromagnetic wave measurement device according to the second embodiment of the present invention.

FIG. 6 is a diagram showing a configuration of the electromagnetic wave measurement device according to the second embodiment of the present invention. The electromagnetic wave measurement device according to the second embodiment includes the electromagnetic wave output device 2, the electromagnetic wave detector 4, the scanning stage (rotational drive unit) 6, the display 8, the image deriving device 10, the incident lens (incident optical system) 22, and the objective lens 24. In the following section, the same components are denoted by the same numerals as of the first embodiment, and will be explained in no more details.

The electromagnetic wave output device 2, the electromagnetic wave detector 4, the scanning stage (rotational drive unit) 6, the display 8, the image deriving device 10, the incident lens (incident optical system) 22, and the objective lens 24 are the same as those of the first embodiment, and a detailed description thereof is, therefore, omitted.

Moreover, a variation may be configured such that the electromagnetic wave output device 2, the incident lens 22, the objective lens 24, and the electromagnetic wave detector 4 are placed on the scanning stage 6 as in the first embodiment, and a detailed description thereof is, therefore, omitted.

It should be noted that the position which gives the minimum value d of the beam diameter of the terahertz wave coincides with the predetermined point of measurement B on the cross section of the DUT 1 in FIG. 6. However, the point of measurement B is different from the intersection between the cross section of the DUT 1 and the line A (rotational axis). In FIG. 6, a distance between the coordinate on the optical axis L of the point of measurement B and the coordinate on the optical axis L of the intersection between the line A and the cross section is denoted by p1.

When the cross section of the DUT 1 on a plane orthogonal to the line A is measured, the movement to the X direction and the rotation about the line A of the scanning stage 6 are carried out at the same time as in the first embodiment. Alternatively, the optical axis L may be moved to the X direction, and may be also rotated about the line A (refer to the variation of the first embodiment (FIG. 13)).

FIGS. 7(a) and 7(b) are plan views of the DUT 1, the electromagnetic wave output device 2, the incident lens 22, the objective lens 24, the electromagnetic wave detector 4, and the scanning stage 6 when the scanning stage 6 is moved to the X direction, and is also rotated about the line A for measuring a cross section of the DUT 1 on a plane orthogonal to the line A according to the second embodiment.

FIG. 7(a) is a plan view when the scanning stage 6 is moved to the +X direction and is also rotated in the +θ direction from the state in FIG. 1. It should be noted that the electromagnetic wave output device 2, the incident lens 22, the objective lens 24, and the electromagnetic wave detector 4 may be moved to the −X direction, and may also be rotated in the −θ direction (which moves the optical axis L to the −X direction, and rotates −θ direction), and this brings about the same state as shown in FIG. 7(a).

A distance between the coordinate on the optical axis L of the point of measurement B and the coordinate on the optical axis L of the intersection between the line A and the cross section is denoted by p2. Then, a relationship p2<p1 holds. On this occasion, the coordinate on the optical axis L of the position which gives the minimum value d of the beam diameter and the coordinate on the optical axis L of the point of measurement B are made coincident with each other. Since a relationship p2≠p1 holds, it is necessary to move the position which gives the minimum value d of the beam diameter or the point of measurement B to the direction of the optical axis L (Y direction) from the state in FIG. 6.

Figure 7:
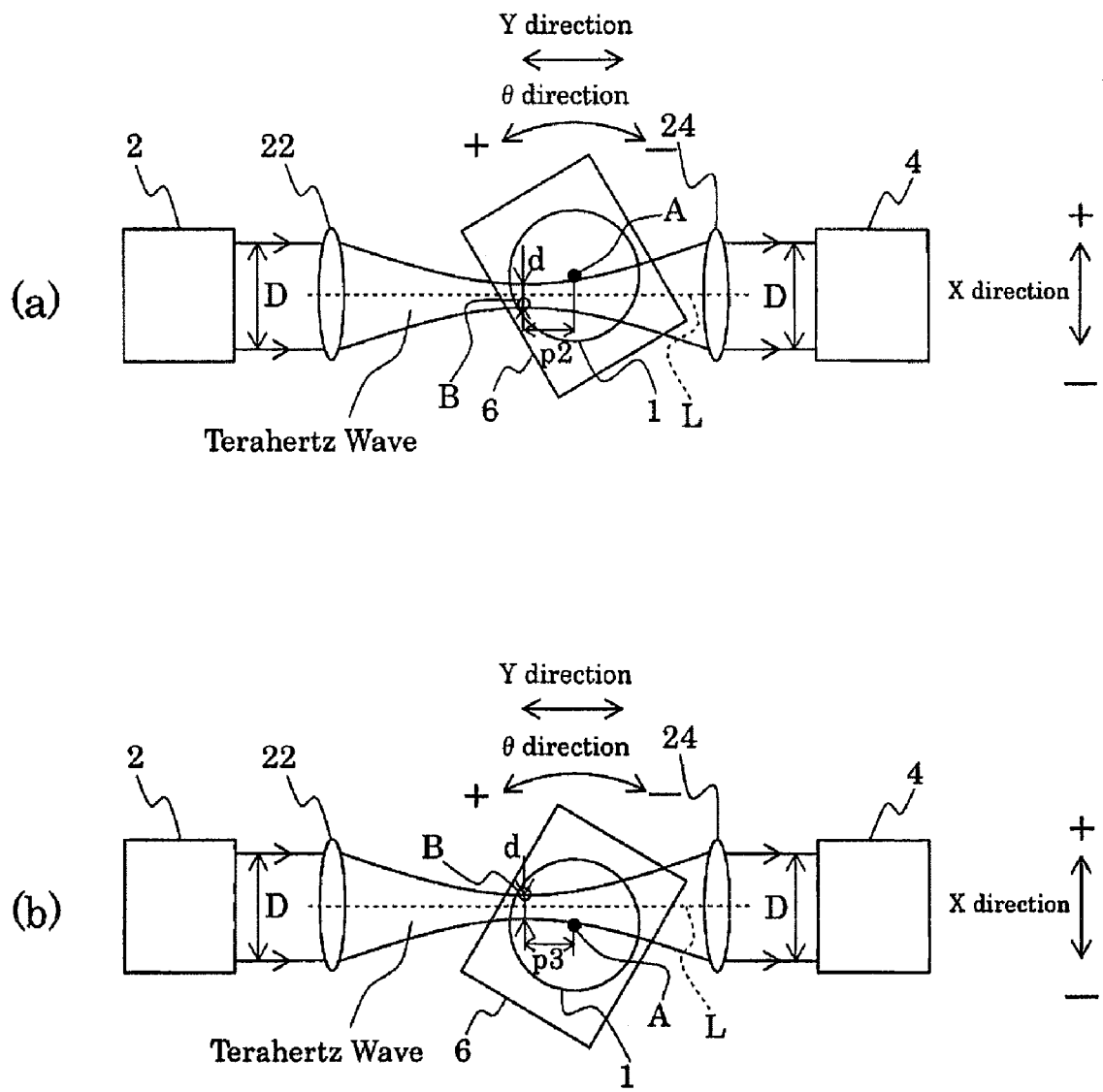
FIGS. 7(a) and 7(b) are plan views of the DUT 1, the electromagnetic wave output device 2, the incident lens 22, the objective lens 24, the electromagnetic wave detector 4, and the scanning stage 6 when the scanning stage 6 is moved to the X direction, and is also rotated about the line A for measuring a cross section of the DUT 1 on a plane orthogonal to the line A according to the second embodiment.

FIG. 7(*b*) is a plan view when the scanning stage 6 is moved to the −X direction and is also rotated in the −θ direction from the state in FIG. 1. It should be noted that the electromagnetic wave output device 2, the incident lens 22, the objective lens 24, and the electromagnetic wave detector 4 may be moved to the +X direction, and may also be rotated in the +θ direction (which moves the optical axis L to the +X direction, and rotates +θ direction), and this brings about the same state as shown in FIG. 7(*b*).

A distance between the coordinate on the optical axis L of the point of measurement B and the coordinate on the optical axis L of the line A is denoted by p3. Then, a relationship p3<p1 holds. On this occasion, the coordinate on the optical axis L of the position which gives the minimum value d of the beam diameter and the coordinate on the optical axis L of the point of measurement B are made coincident with each other. Since a relationship p3≠p1 holds, it is necessary to move the position which gives the minimum value d of the beam diameter or the point of measurement B to the direction of the optical axis L (Y direction) from the state in FIG. 6.

For example, the point of measurement B is moved along with the DUT 1 to the Y direction by moving the scanning stage 6 to the Y direction, thereby it is possible to make the coordinate on the optical axis L of the position which gives the minimum value d of the beam diameter and the coordinate on the optical axis L of the point of measurement B coincident with each other.

Moreover, the position which gives the minimum value d of the beam diameter is moved to the Y direction by moving the incident lens 22 to the Y direction, thereby it is possible to make the coordinate on the optical axis L of the position which gives the minimum value d of the beam diameter and the coordinate on the optical axis L of the point of measurement B coincident with each other.

Further, the position which gives the minimum value d of the beam diameter is moved to the Y direction by changing the focal distance of the incident lens 22 (it is assumed that the position which gives the minimum value d of the beam diameter is the focal point), thereby it is possible to make the coordinate on the optical axis L of the position which gives the minimum value d of the beam diameter and the coordinate on the optical axis L of the point of measurement B coincident with each other.

It should be noted that the position which gives the minimum value d of the beam diameter is coincident with the point of measurement B in FIGS. 7(*a*) and 7(*b*). However, even if the point of measurement B does not coincide with the position which gives the minimum value d of the beam diameter (namely, the X coordinate of the point of measurement B is out of the range in terms of the X coordinate of the portion which gives the minimum value d of the beam diameter), the coordinate on the optical axis L (Y coordinate) of the position which gives the minimum value d of the beam diameter and the coordinate on the optical axis L (Y coordinate) of the point of measurement B are made coincident with each other.

A description will now be given of an operation of the second embodiment.

First, the DUT 1 is fixed to the scanning stage 6. The position which gives the minimum value d of the beam diameter of the terahertz wave is then made coincident with the predetermined point of measurement B on the cross section of the DUT 1. The scanning stage 6 is then moved to the X direction, and is also rotated about the line A.

On this occasion, the electromagnetic wave having the frequency equal to or more than 0.01 [THz] and equal to or less than 100 [THz] (such as the terahertz wave) is output from the electromagnetic wave output device 2 toward the DUT 1. The terahertz wave output toward the DUT 1 is made incident to the DUT 1 while the beam diameter is decreased by the incident lens 22.

On this occasion, the coordinate on the optical axis L of the position which gives the minimum value d of the beam diameter and the coordinate on the optical axis L of the point of measurement B are made coincident with each other (refer to FIGS. 7(*a*) and 7(*b*)). For example, the point of measurement B is moved to the Y direction by moving the scanning stage 6 to the Y direction, thereby making both of the coordinates coincident with each other. For example, the position which gives the minimum value d of the beam diameter is moved to the Y direction by moving the incident lens 22 to the Y direction (or changing the focal distance of the incident lens 22), thereby making both of the coordinates coincident with each other.

On this occasion, referring to FIGS. 7(*a*) and 7(*b*), the position which gives the minimum value d of the beam diameter of the terahertz wave is often close to the point of measurement B whether the scanning stage 6 moves or rotates.

The terahertz wave transmits through the DUT 1, the beam diameter gradually increases from d, and the terahertz wave is made incident to the objective lens 24. The objective lens 24 changes the beam diameter of the terahertz wave which has transmitted through the DUT 1 to a constant value (such as D), and makes the terahertz wave incident to the electromagnetic wave detector 4.

The electromagnetic wave which has transmitted through the DUT 1 is detected via the objective lens 24 by the electromagnetic wave detector 4. In this way, the DUT 1 is scanned.

The result detected by the electromagnetic wave detector 4 is fed to the image deriving device 10, and derives the image of the cross section of the DUT 1 on the plane orthogonal to the line A. The image derived by the image deriving device 10 is shown by the display 8.

When a certain cross section of the DUT 1 has been measured, the scanning stage 6 is moved to the direction of the line A by a predetermined distance, and is fixed, and the DUT 1 is scanned for measurement of a further cross section.

According to the second embodiment, the position which gives the minimum value d of the beam diameter can often coincide with the point of measurement B. Moreover, the position which gives the minimum value d of the beam diameter of the terahertz wave is a position having a high spatial resolution for measuring the cross section. Thus, the spatial resolution can be increased for the measurement of the point of measurement B.

Third Embodiment

The electromagnetic wave measurement device according to the third embodiment is approximately the same as a case in which multiple distances p (refer to FIG. 1) are provided in the electromagnetic wave measurement device according to the first embodiment. However, the distance p here is different from the distance p according to the first embodiment, and is free from a restriction such as 0.3 r≦p≦0.7 r (may be zero, for example).

Figure 8:
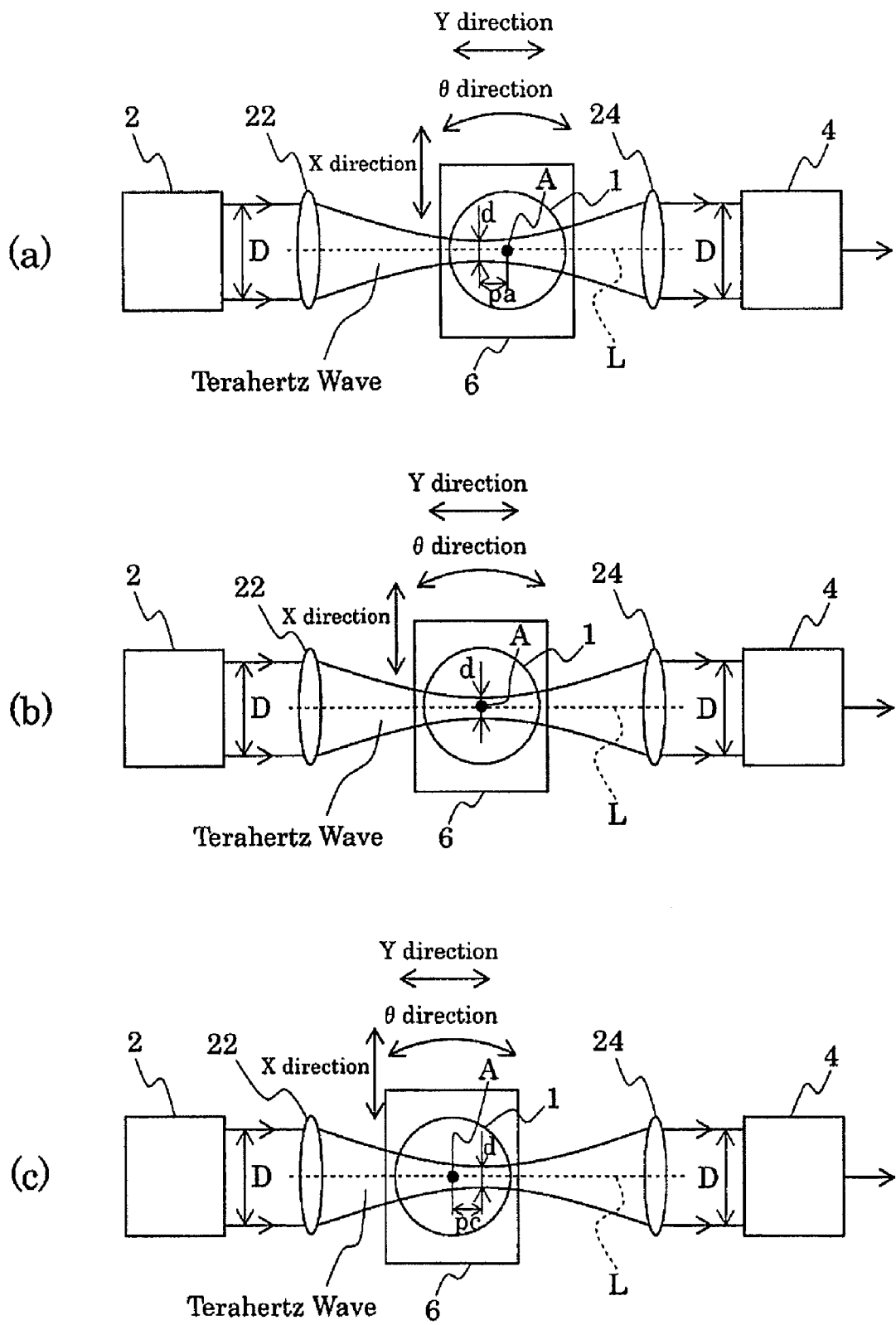
FIGS. 8(a), 8(b), and 8(c) are diagrams showing a configuration of the electromagnetic wave measurement device according to the third embodiment of the present invention.

FIGS. 8(*a*), 8(*b*), and 8(*c*) are diagrams showing a configuration of the electromagnetic wave measurement device according to the third embodiment of the present invention. The electromagnetic wave measurement device according to the third embodiment includes the electromagnetic wave output device 2, the electromagnetic wave detector 4, the scanning stage (rotational drive unit) 6, the display 8, the image deriving device 10, the incident lens (incident optical system) 22, and the objective lens 24. The electromagnetic wave measurement device is used for measuring the DUT 1. However, the display 8 and the image deriving device 10 are the same as those in FIG. 1, and are thus not shown in FIG. 8.

In the electromagnetic wave measurement device according to the third embodiment of the present invention, there are set three types of distances pa (refer to FIG. 8(a)), 0 (refer to FIG. 8(b)), and pc (refer to FIG. 8(c)) between the coordinate on the optical axis L which gives the minimum value d of the beam diameter of the terahertz wave and the coordinate on the optical axis L of the line A (rotational axis). It should be noted that the number of the types of the distance is not limited to three, may be two or more, and are preferably approximately 16, for example.

In FIG. 8(a), the coordinate on the optical axis L of the position which gives the minimum value d of the beam diameter is −pa when the coordinate on the optical axis L of the line A (rotational axis) is the origin. It should be noted that a relationship 0<pa<r holds. The configuration of the electromagnetic wave measurement device in FIG. 8(a) is the same as that of the electromagnetic wave measurement device according to the first embodiment (and the variation thereof (FIG. 13)) except that the distance between the coordinate on the optical axis L of the position which gives the minimum value d of the beam diameter of the terahertz wave and the coordinate on the optical axis L of the line A (rotational axis) is pa. For example, the incident lens 22, the scanning stage 6, and the electromagnetic wave detector 4 are the same as those of the first embodiment.

In FIG. 8(b), the coordinate on the optical axis L of the position which gives the minimum value d of the beam diameter is zero when the coordinate on the optical axis L of the line A (rotational axis) is the origin. The configuration of the electromagnetic wave measurement device in FIG. 8(b) is the same as that of the electromagnetic wave measurement device according to the first embodiment (and the variation thereof (FIG. 13)) except that the distance between the coordinate on the optical axis L of the position which gives the minimum value d of the beam diameter of the terahertz wave and the coordinate on the optical axis L of the line A (rotational axis) is zero. For example, the incident lens 22, the scanning stage 6, and the electromagnetic wave detector 4 are the same as those of the first embodiment.

In FIG. 8(c), the coordinate on the optical axis L of the position which gives the minimum value d of the beam diameter is pc when the coordinate on the optical axis L of the line A (rotational axis) is the origin. It should be noted that a relationship 0<pc<r holds. The configuration of the electromagnetic wave measurement device in FIG. 8(c) is the same as that of the electromagnetic wave measurement device according to the first embodiment (and the variation thereof (FIG. 13)) except that the distance between the coordinate on the optical axis L of the position which gives the minimum value d of the beam diameter of the terahertz wave and the coordinate on the optical axis L of the line A (rotational axis) is pc. For example, the incident lens 22, the scanning stage 6, and the electromagnetic wave detector 4 are the same as those of the first embodiment.

However, in the electromagnetic wave measurement device according to the third embodiment, the cross section of the DUT 1 on the plane orthogonal to the line A (rotational axis) is measured based on results detected by the electromagnetic wave detector 4 for the respective types of the coordinate (refer to FIGS. 8(a), 8(b), and 8(c)).

In other words, the image deriving device 10 of the electromagnetic wave measurement device according to the third embodiment derives the image of the cross section of the DUT 1 based on results detected by the electromagnetic wave detector 4 for the respective types of the coordinate (refer to FIGS. 8(a), 8(b), and 8(c)).

A description will now be given of an operation of the third embodiment.

It should be noted that the distance between the coordinate on the optical axis L of the position which gives the minimum value d of the beam diameter of the terahertz wave and the coordinate on the optical axis L of the line A (rotational axis) is sometimes referred to as offset hereinafter.

(1) Measurement for Offset pa (Refer to FIG. 8(a))

First, the DUT 1 is fixed to the scanning stage 6. Then, the scanning stage 6 is not moved to the direction of the line A, but is fixed, and is moved to the Y direction, and the DUT 1 is moved to the Y direction so that the distance between the coordinate on the optical axis L of the position which gives the minimum value d of the beam diameter of the terahertz wave and the coordinate on the optical axis L of the line A (rotational axis) is pa (refer to FIG. 8(a)). It should be noted that the offset may be set to pa by moving the incident lens 22 to the Y direction (or by changing the focal distance of the incident lens 22).

The scanning stage 6 is then moved to the X direction, and is also rotated about the line A. As a result, the DUT 1 is moved to the X direction (the direction orthogonal to the optical axis L and the line A (rotational axis)), and also rotated about the line A. Alternatively, the optical axis L is moved to the X direction, and is also rotated about the line A (refer to the variation of the first embodiment (FIG. 13)).

On this occasion, the electromagnetic wave having the frequency equal to or more than 0.01 [THz] and equal to or less than 100 [THz] (such as the terahertz wave) is output from the electromagnetic wave output device 2 toward the DUT 1. The terahertz wave output toward the DUT 1 is made incident to the DUT 1 while the beam diameter is decreased by the incident lens 22.

On this occasion, the position which gives the minimum value d of the beam diameter of the terahertz wave moves to a certain portion (referred to as "portion a" tentatively) on the cross section of the DUT 1 as the scanning stage 6 moves and rotates.

The terahertz wave transmits through the DUT 1, the beam diameter gradually increases from d, and the terahertz wave is made incident to the objective lens 24. The objective lens 24 changes the beam diameter of the terahertz wave which has transmitted through the DUT 1 to a constant value (such as D), and makes the terahertz wave incident to the electromagnetic wave detector 4.

The electromagnetic wave which has transmitted through the DUT 1 is detected via the objective lens 24 by the electromagnetic wave detector 4. In this way, the DUT 1 is scanned.

The result detected by the electromagnetic wave detector 4 is fed to the image deriving device 10. The result detected by the electromagnetic wave detector 4 is high in spatial resolution in the "portion a".

(2) Measurement for Offset Zero (Refer to FIG. 8(b))

Then, the scanning stage 6 is not moved to the direction of the line A, but is fixed, and is moved to the Y direction, and the DUT 1 is moved to the Y direction so that the distance between the coordinate on the optical axis L of the position which gives the minimum value d of the beam diameter of the terahertz wave and the coordinate on the optical axis L of the line A (rotational axis) is zero (refer to FIG. 8(b)). It should be noted that the offset may be set to zero by moving the incident lens 22 to the Y direction (or by changing the focal distance of the incident lens 22).

The scanning stage 6 is then moved to the X direction, and is also rotated about the line A. As a result, the DUT 1 is moved to the X direction (the direction orthogonal to the optical axis L and the line A (rotational axis)), and also rotated about the line A. Alternatively, the optical axis L is moved to the X direction, and is also rotated about the line A (refer to the variation of the first embodiment (FIG. 13)).

On this occasion, the electromagnetic wave having the frequency equal to or more than 0.01 [THz] and equal to or less than 100 [THz] (such as the terahertz wave) is output from the electromagnetic wave output device 2 toward the DUT 1. The terahertz wave output toward the DUT 1 is made incident to the DUT 1 while the beam diameter is decreased by the incident lens 22.

On this occasion, the position which gives the minimum value d of the beam diameter of the terahertz wave moves to a certain portion (referred to as "portion b" tentatively) on the cross section of the DUT 1 as the scanning stage 6 moves and rotates.

The terahertz wave transmits through the DUT 1, the beam diameter gradually increases from d, and the terahertz wave is made incident to the objective lens 24. The objective lens 24 changes the beam diameter of the terahertz wave which has transmitted through the DUT 1 to a constant value (such as D), and makes the terahertz wave incident to the electromagnetic wave detector 4.

The electromagnetic wave which has transmitted through the DUT 1 is detected via the objective lens 24 by the electromagnetic wave detector 4. In this way, the DUT 1 is scanned.

The result detected by the electromagnetic wave detector 4 is fed to the image deriving device 10. The result detected by the electromagnetic wave detector 4 is high in spatial resolution in the "portion b".

(3) Measurement for Offset pc (Refer to FIG. 8(c))

Then, the scanning stage 6 is not moved to the direction of the line A, but is fixed, and is moved to the Y direction, and the DUT 1 is moved to the Y direction so that the distance between the coordinate on the optical axis L of the position which gives the minimum value d of the beam diameter of the terahertz wave and the coordinate on the optical axis L of the line A (rotational axis) is pc (refer to FIG. 8(c)). It should be noted that the offset may be set to pc by moving the incident lens 22 to the Y direction (or by changing the focal distance of the incident lens 22).

The scanning stage 6 is then moved to the X direction, and is also rotated about the line A. As a result, the DUT 1 is moved to the X direction (the direction orthogonal to the optical axis L and the line A (rotational axis)), and also rotated about the line A. Alternatively, the optical axis L is moved to the X direction, and is also rotated about the line A (refer to the variation of the first embodiment (FIG. 13)).

On this occasion, the electromagnetic wave having the frequency equal to or more than 0.01 [THz] and equal to or less than 100 [THz] (such as the terahertz wave) is output from the electromagnetic wave output device 2 toward the DUT 1. The terahertz wave output toward the DUT 1 is made incident to the DUT 1 while the beam diameter is decreased by the incident lens 22.

On this occasion, the position which gives the minimum value d of the beam diameter of the terahertz wave moves to a certain portion (referred to as "portion c" tentatively) on the cross section of the DUT 1 as the scanning stage 6 moves and rotates.

The terahertz wave transmits through the DUT 1, the beam diameter gradually increases from d, and the terahertz wave is made incident to the objective lens 24. The objective lens 24 changes the beam diameter of the terahertz wave which has transmitted through the DUT 1 to a constant value (such as D), and makes the terahertz wave incident to the electromagnetic wave detector 4.

The electromagnetic wave which has transmitted through the DUT 1 is detected via the objective lens 24 by the electromagnetic wave detector 4. In this way, the DUT 1 is scanned.

The result detected by the electromagnetic wave detector 4 is fed to the image deriving device 10. The result detected by the electromagnetic wave detector 4 is that the spatial resolution is high in the "portion c".

It should be noted that the "portions a, b, and c" are different from each other.

(4) Derivation and Display of Image

On this occasion, the image deriving device 10 derives an image for the "portion a" and a neighborhood thereof out of the cross section on the plane orthogonal to the line A of the DUT 1 based on the result detected by the electromagnetic wave detector 4 in "(1) Measurement for offset pa". The derivation of the image may be based on the derivation of an image by the widely-known filtered back-projection.

Moreover, the image deriving device 10 derives an image for the "portion b" and a neighborhood thereof out of the cross section on the plane orthogonal to the line A of the DUT 1 based on the result detected by the electromagnetic wave detector 4 in "(2) Measurement for offset zero". The derivation of the image may be based on the derivation of an image by the widely-known filtered back-projection.

Further, the image deriving device 10 derives an image for the "portion c" and a neighborhood thereof out of the cross section on the plane orthogonal to the line A of the DUT 1 based on the result detected by the electromagnetic wave detector 4 in "(3) Measurement for offset pc". The derivation of the image may be based on the derivation of an image by the widely-known filtered back-projection.

It should be noted that a portion other than the "portions a, b, and c" out of the cross section on the plane orthogonal to the line A of the DUT 1 is contained in the neighborhoods of any one of the "portions a, b, and c".

The image deriving device 10 composes the images derived in this way, thereby deriving an image of the cross section of the DUT 1 on the plane orthogonal to the line A. The image derived by the image deriving device 10 is shown by the display 8.

When the measurement of a certain cross section of the DUT 1 has been completed, the scanning stage 6 is moved to the direction of the line A by a predetermined distance, and is fixed, and the DUT 1 is scanned for measurement of a further cross section.

According to the third embodiment, the measurement can be carried out at the high spatial resolution in the neighborhood of the "portion a". Moreover, the measurement can be carried out at the high spatial resolution in the neighborhood of the "portion b", which is other than the neighborhood of the "portion a". Further, the measurement can be carried out at the high spatial resolution in the neighborhood of the "portion c", which is other than the neighborhood of the "portion a" and the neighborhood of the "portion b".

As a result, a cross section can be measured at the high spatial resolution compared with the measurement in any one of the configurations shown in FIGS. 8(a), 8(b), and 8(c).

For example, when the measurement is carried out in the configuration shown in FIG. 8(b) (corresponding to the conventional CT), the measurement can be carried out at the high spatial resolution only in the neighborhood of the "portion b". However, even when a portion is not in the neighborhood of the "portion b", the measurement at the high spatial resolution can be carried out as long as the portion is in the neighborhoods of the "portions a and c" according to the third embodiment.

When more types of the distance between the coordinate on the optical axis L of the position which gives the minimum value d of the beam diameter of the terahertz wave and the coordinate on the optical axis L of the line A (rotational axis) are set, a more precise measurement can be carried out on the cross section. However, if more types of the distance are set, a period required for the measurement increases, and the number of types is preferably set to 16, for example, as described above.

Fourth Embodiment

The electromagnetic wave measurement device according to a fourth embodiment corresponds to the electromagnetic wave measurement device according to the third embodiment which does not rotate the DUT 1.

Figure 9:
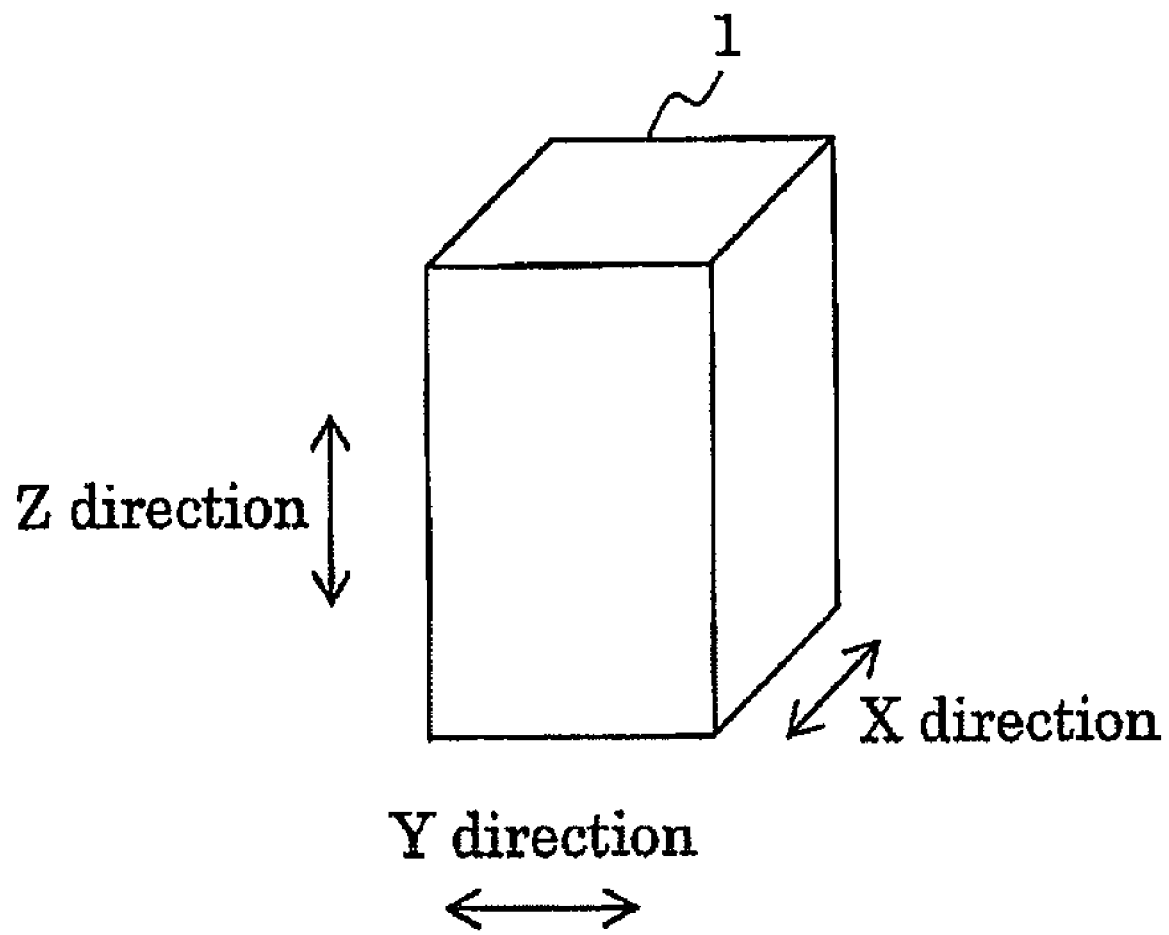
FIG. 9 is a perspective view of the DUT 1 according to the fourth embodiment of the present invention.

FIG. 9 is a perspective view of the DUT 1 according to the fourth embodiment of the present invention. The DUT 1 is a rectangular solid, and the X, Y, and Z directions are defined as illustrated. It should be noted that the Y direction is the direction in which the optical axis L extends as described later. The X and Z directions are orthogonal to the optical axis L, and are orthogonal to each other.

Figure 10:
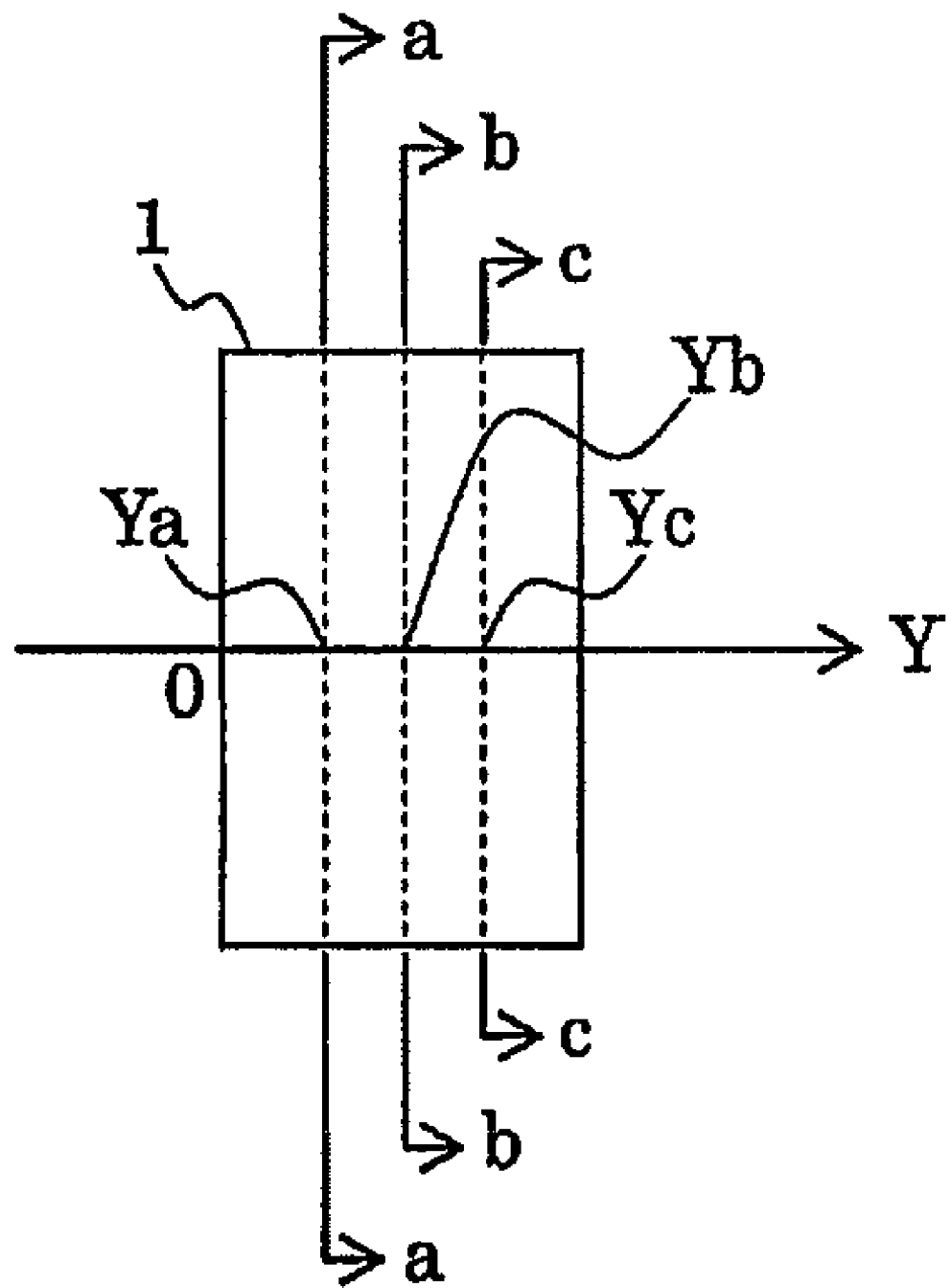
FIG. 10 is a front view of the DUT 1 according to the fourth embodiment of the present invention.

FIG. 10 is a front view of the DUT 1 according to the fourth embodiment of the present invention. The electromagnetic wave measurement device according to the fourth embodiment measures an a-a cross section (Y coordinate: Ya), a b-b cross section (Y coordinate: Yb), and a c-c cross section (Y coordinate: Yc) of the DUT 1. It should be noted that the origin of the Y coordinate is the Y coordinate of a left side surface (predetermined part) of the DUT 1.

Figure 11:
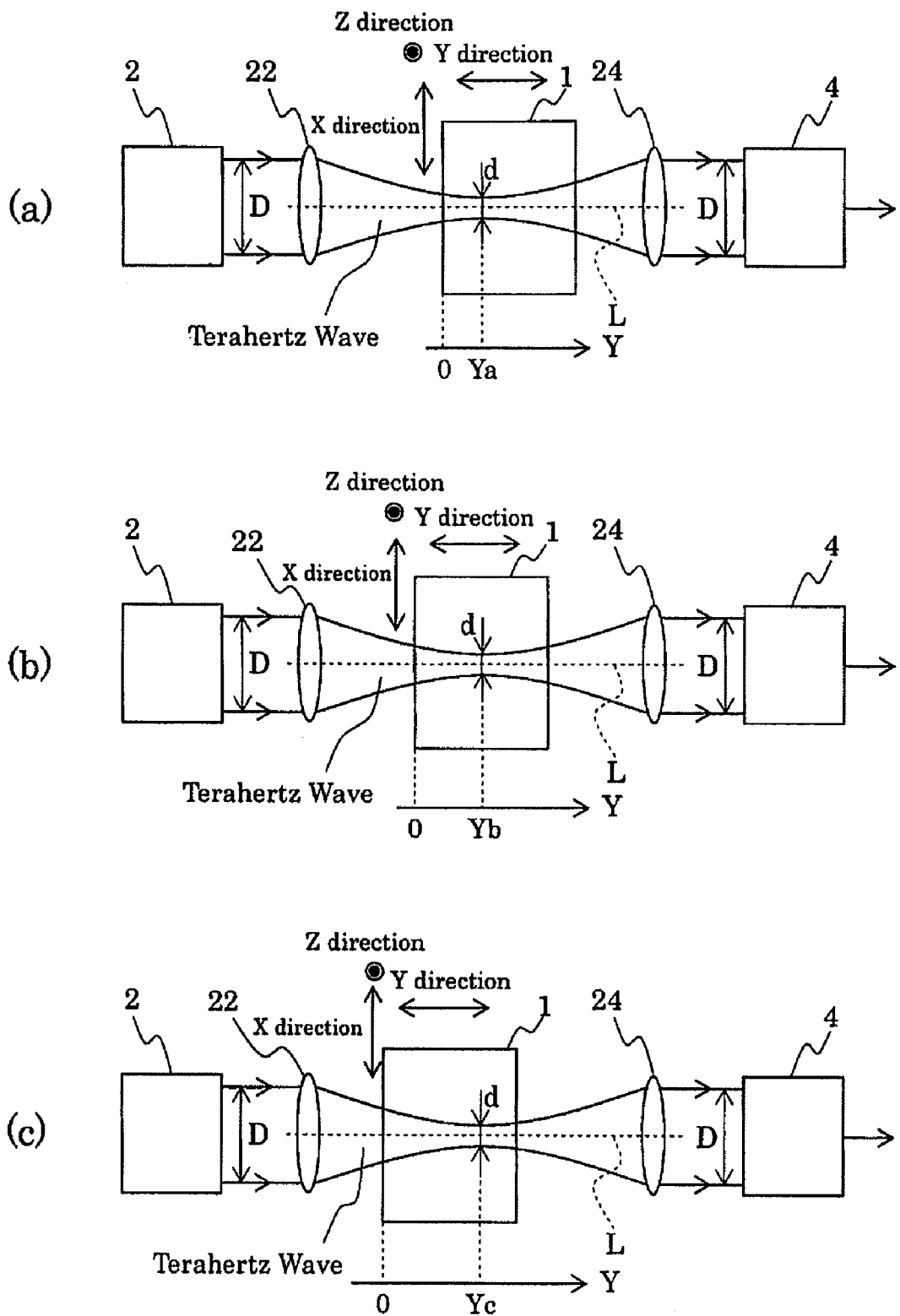
FIGS. 11(a) to 11(c) are diagrams showing a configuration of the electromagnetic wave measurement device according to the fourth embodiment of the present invention.

FIGS. 11(a) to 11(c) are diagrams showing a configuration of the electromagnetic wave measurement device according to the fourth embodiment of the present invention. The electromagnetic wave measurement device according to the fourth embodiment includes the electromagnetic wave output device 2, the electromagnetic wave detector 4, the display 8, the image deriving device 10, the incident lens (incident optical system) 22, and the objective lens 24. The electromagnetic wave measurement device is used for measuring the DUT 1. However, the display 8 and the image deriving device 10 are the same as those in FIG. 1, and are thus not shown in FIGS. 11(a) to 11(c). In the following section, the same components are denoted by the same numerals as of the first embodiment, and will be explained in no more details.

The electromagnetic wave output device 2, the electromagnetic wave detector 4, the display 8, the incident lens (incident optical system) 22, and the objective lens 24 are the same as those of the first embodiment, and a detailed description is, therefore, omitted. It should be noted that the DUT 1 can be moved to the X, Y, and Z directions by drive mechanisms, which are not shown. It should be noted that the Y direction is the direction in which the optical axis L extends. Alternatively, the optical axis L may be moved to the X, Y, and Z directions.

The a-a, b-b, and c-c cross sections to be measured are cross sections orthogonal to the optical axis L.

A description will now be given of an operation of the fourth embodiment.

(1) Measurement of a-a Cross Section (Refer to FIG. 11(a))

The DUT 1 or the incident lens 22 is moved to the Y direction (or the focal distance of the incident lens 22 is changed), thereby making the coordinate on the optical axis L of the position which gives the minimum value d of the beam diameter of the terahertz wave coincident with Ya. On this occasion, the DUT 1 or the optical axis L is moved to the X and Z directions which are orthogonal to the optical axis L and to each other.

Then, the electromagnetic wave having the frequency equal to or more than 0.01 [THz] and equal to or less than 100 [THz] (such as the terahertz wave) is output from the electromagnetic wave output device 2 toward the DUT 1. The terahertz wave output toward the DUT 1 is made incident to the DUT 1 while the beam diameter is decreased by the incident lens 22.

The position which gives the minimum value d of the beam diameter presents a high spatial resolution, and is the a-a cross section. The terahertz wave is irradiated on the entire a-a cross section by moving the DUT 1 or the optical axis L to the X and Z directions.

The terahertz wave transmits through the DUT 1, the beam diameter gradually increases from d, and the terahertz wave is made incident to the objective lens 24. The objective lens 24 changes the beam diameter of the terahertz wave which has transmitted through the DUT 1 to a constant value (such as D), and makes the terahertz wave incident to the electromagnetic wave detector 4.

The electromagnetic wave which has transmitted through the DUT 1 is detected via the objective lens 24 by the electromagnetic wave detector 4. In this way, the a-a cross section of the DUT 1 is scanned.

The result detected by the electromagnetic wave detector 4 is fed to the image deriving device 10. The image deriving device 10 derives an image of the a-a cross section (which corresponds to a measurement of the a-a cross section). The a-a image derived by the image deriving device 10 is shown by the display 8.

(2) Measurement of b-b Cross Section (Refer to FIG. 11(b))

The DUT 1 or the incident lens 22 is moved to the Y direction (or the focal distance of the incident lens 22 is changed), thereby making the coordinate on the optical axis L of the position which gives the minimum value d of the beam diameter of the terahertz wave coincident with Yb. On this occasion, the DUT 1 or the optical axis L is moved to the X and Z directions which are orthogonal to the optical axis L and to each other.

Then, the electromagnetic wave having the frequency equal to or more than 0.01 [THz] and equal to or less than 100 [THz] (such as the terahertz wave) is output from the electromagnetic wave output device 2 toward the DUT 1. The terahertz wave output toward the DUT 1 is made incident to the DUT 1 while the beam diameter is decreased by the incident lens 22.

The position which gives the minimum value d of the beam diameter presents a high spatial resolution, and is the b-b cross section. The terahertz wave is irradiated on the entire b-b cross section by moving the DUT 1 or the optical axis L to the X and Z directions.

The terahertz wave transmits through the DUT 1, the beam diameter gradually increases from d, and the terahertz wave is made incident to the objective lens 24. The objective lens 24 changes the beam diameter of the terahertz wave which has transmitted through the DUT 1 to a constant value (such as D), and makes the terahertz wave incident to the electromagnetic wave detector 4.

The electromagnetic wave which has transmitted through the DUT 1 is detected via the objective lens 24 by the electromagnetic wave detector 4. In this way, the b-b cross section of the DUT 1 is scanned.

The result detected by the electromagnetic wave detector 4 is fed to the image deriving device 10. The image deriving device 10 derives an image of the b-b cross section (which corresponds to a measurement of the b-b cross section). The b-b image derived by the image deriving device 10 is shown by the display 8.

(3) Measurement of c-c Cross Section (Refer to FIG. 11(c))

The DUT 1 or the incident lens 22 is moved to the Y direction (or the focal distance of the incident lens 22 is changed), thereby making the coordinate on the optical axis L of the position which gives the minimum value d of the beam diameter of the terahertz wave coincident with Yc. On this occasion, the DUT 1 or the optical axis L is moved to the X and Z directions which are orthogonal to the optical axis L and to each other.

Then, the electromagnetic wave having the frequency equal to or more than 0.01 [THz] and equal to or less than 100 [THz] (such as the terahertz wave) is output from the electromagnetic wave output device 2 toward the DUT 1. The terahertz wave output toward the DUT 1 is made incident to the DUT 1 while the beam diameter is decreased by the incident lens 22.

The position which gives the minimum value d of the beam diameter presents a high spatial resolution, and is the c-c cross section. The terahertz wave is irradiated on the entire c-c cross section by moving the DUT 1 or the optical axis L to the X and Z directions.

The terahertz wave transmits through the DUT 1, the beam diameter gradually increases from d, and the terahertz wave is made incident to the objective lens 24. The objective lens 24 changes the beam diameter of the terahertz wave which has transmitted through the DUT 1 to a constant value (such as D), and makes the terahertz wave incident to the electromagnetic wave detector 4.

The electromagnetic wave which has transmitted through the DUT 1 is detected via the objective lens 24 by the electromagnetic wave detector 4. In this way, the c-c cross section of the DUT 1 is scanned.

The result detected by the electromagnetic wave detector 4 is fed to the image deriving device 10. The image deriving device 10 derives an image of the c-c cross section (which corresponds to a measurement of the c-c cross section). The c-c image derived by the image deriving device 10 is shown by the display 8.

As described above, the number of types of the coordinate on the optical axis L of the position which gives the minimum value d of the beam diameter of the terahertz wave is set three, Ya, Yb, and Yc (as long as the number is multiple, the number is not limited to three), images of the a-a cross section, b-b cross section, and c-c cross section are derived based on the results detected by the electromagnetic wave detector 4 at the respective coordinates (which corresponds to the measurement of the DUT 1).

According to the fourth embodiment, it is possible to increase the spatial resolution for measuring the XZ cross section of the DUT 1 which is a rectangular solid and has a thickness in the Y direction.

The invention claimed is:

1. An electromagnetic wave measurement device comprising:
    an incident optical system that makes an electromagnetic wave to be measured having a frequency equal to or more than 0.01 THz and equal to or less than 100 THz incident to a device under test while decreasing a beam diameter of the electromagnetic wave to be measured;
    a rotational driver that rotates, about a line orthogonal to an optical axis of the incident optical system as a rotational axis, the device under test or the optical axis; and
    an electromagnetic wave detector that detects the electromagnetic wave to be measured which has transmitted through the device under test,
    wherein a coordinate on the optical axis of a position at which the beam diameter is a minimum is different from a coordinate on the optical axis of the rotational axis.

2. The electromagnetic wave measurement device according to claim 1, wherein a relationship $0.3 \leq p \leq 0.7r$ is satisfied, where r denotes a radius of a cross section of the device under test on a plane orthogonal to the rotational axis, and p denotes a distance between the coordinate on the optical axis of the position at which the beam diameter is the minimum, and the coordinate on the optical axis of the rotational axis.

3. The electromagnetic wave measurement device according to claim 2, wherein a relationship $p=0.5r$ is satisfied.

4. The electromagnetic wave measurement device according to claim 1, wherein:
    a cross section of the device under test on a plane orthogonal to the rotational axis is to be measured; and
    when p denotes a distance between the coordinate on the optical axis of the position at which the beam diameter is the minimum, and the coordinate on the optical axis of the rotational axis, p is determined so that the spatial resolution upon the measurement of the cross section takes a desired value over the entire cross section.

5. The electromagnetic wave measurement device according to claim 1, wherein:
    a cross section of the device under test on a plane orthogonal to the rotational axis is to be measured; and
    a coordinate on the optical axis of a predetermined point of measurement on the cross section, which is different from an intersection between the cross section and the rotational axis, and the coordinate on the optical axis of the position at which the beam diameter is the minimum are made to coincide with each other.

6. The electromagnetic wave measurement device according to claim 1, wherein the incident optical system can be moved in a direction of the optical axis.

7. The electromagnetic wave measurement device according to claim 1, wherein the device under test can be moved in a direction of the optical axis.

8. The electromagnetic wave measurement device according to claim 1, wherein a focal distance of the incident optical system can be changed.

9. The electromagnetic wave measurement device according to claim 1, wherein:
    a cross section of the device under test on a plane orthogonal to the rotational axis is to be measured; and
    the cross section is measured while the device under test or the optical axis is moved to in a direction orthogonal to the optical axis and the rotational axis.

10. An electromagnetic wave measurement device comprising:
    an incident optical system that makes an electromagnetic wave to be measured having a frequency equal to or more than 0.01 THz and equal to or less than 100 THz incident to a device under test while decreasing a beam diameter of the electromagnetic wave to be measured;

a rotational driver that rotates, about a line orthogonal to an optical axis of the incident optical system as a rotational axis, the device under test or the optical axis; and an electromagnetic wave detector that detects the electromagnetic wave to be measured which has transmitted through the device under test, wherein:

a plurality of types of a coordinate on the optical axis of a position at which the beam diameter is the minimum are set when a coordinate on the optical axis of the rotational axis is an origin; and the device under test is measured based on a result detected by the electromagnetic wave detector at the respective types of the coordinate.

11. The electromagnetic wave measurement device according to claim 10, wherein the incident optical system can be moved in a direction of the optical axis.

12. The electromagnetic wave measurement device according to claim 10, wherein the device under test can be moved in a direction of the optical axis.

13. The electromagnetic wave measurement device according to claim 10, wherein a focal distance of the incident optical system can be changed.

14. The electromagnetic wave measurement device according to claim 10, wherein:

a cross section of the device under test on a plane orthogonal to the rotational axis is to be measured; and the cross section is measured while the device under test or the optical axis is moved in a direction orthogonal to the optical axis and the rotational axis.

* * * * *